(12) United States Patent
Ishihara et al.

(10) Patent No.: US 7,026,409 B2
(45) Date of Patent: Apr. 11, 2006

(54) POLYMER-SUPPORTED ARYLBIS(PERFLUOROALKYLSULFONYL)-METHANE

(75) Inventors: Kazuaki Ishihara, Konan (JP); Hisashi Yamamoto, Chicago, IL (US)

(73) Assignee: Japan Science and Technology Agency, Saitama (JP)

( * ) Notice: Subject to any disclaimer, the term of this patent is extended or adjusted under 35 U.S.C. 154(b) by 158 days.

(21) Appl. No.: 10/471,447

(22) PCT Filed: Mar. 12, 2002

(86) PCT No.: PCT/JP02/02309

§ 371 (c)(1),
(2), (4) Date: Sep. 10, 2003

(87) PCT Pub. No.: WO02/072643

PCT Pub. Date: Sep. 19, 2002

(65) Prior Publication Data

US 2004/0116617 A1 Jun. 17, 2004

(30) Foreign Application Priority Data

Mar. 12, 2001 (JP) .............................. 2001-68985
Sep. 18, 2001 (JP) .............................. 2001-283218

(51) Int. Cl.
*C08C 19/20* (2006.01)

(52) U.S. Cl. ................ 525/353; 525/333.3; 525/333.4; 525/333.5; 525/343

(58) Field of Classification Search ............. 525/333.3, 525/333.4, 333.5, 343, 353
See application file for complete search history.

(56) References Cited

U.S. PATENT DOCUMENTS

| | | | |
|---|---|---|---|
| 4,049,861 A * | 9/1977 | Nozari | 428/220 |
| 4,069,368 A * | 1/1978 | Deyak et al. | 428/447 |
| 4,115,295 A * | 9/1978 | Robins et al. | 528/90 |
| 4,337,107 A | 6/1982 | Eshleman et al. | |
| 4,431,845 A | 2/1984 | Young et al. | |
| 4,830,847 A | 5/1989 | Benedict et al. | 424/1.1 |
| 5,071,737 A | 12/1991 | Kita et al. | |
| 5,932,511 A | 8/1999 | Harmer et al. | |
| 2004/0030192 A1 | 2/2004 | Ishihara et al. | |
| 2005/0070741 A1 | 3/2005 | Ishihara et al. | |

FOREIGN PATENT DOCUMENTS

| | | |
|---|---|---|
| EP | 0 386 930 A1 | 9/1990 |
| EP | 0 985 662 A2 | 3/2000 |
| EP | 1 375 532 A | 1/2004 |
| GB | 2 285 442 A | 7/1995 |
| JP | 03-254697 | 11/1991 |
| JP | 07 246338 A | 9/1995 |
| WO | WO 00/44495 A | 8/2000 |

OTHER PUBLICATIONS

English translation of the International Preliminary Examination Report (Form PCT/IPEA/409), and Notification of Transmittal (Form PCT/IB/338); mailed Dec. 5, 2003, from the International Bureau.
Patent Abstracts of Japan, English abstract of JP 07 246338A, Sep. 26, 1995.
Patent Abstracts of Japan, English abstract of JP 03 254697, Nov. 1991.
Nagayama et al, "A Novel Polymer-Supported Scandium Catalyst Which Shows High Activity in Water," Angewandte Chemie International Edition, vol. 39, No. 3, Feb. 1, 2000, pp. 567-569.

(Continued)

*Primary Examiner*—Helen L. Pezzuto
(74) *Attorney, Agent, or Firm*—Morgan & Finnegan, L.L.P.; Kenneth H. Sonnenfeld; Michael A. Willis

(57) ABSTRACT

The present invention provides a solid acid catalyst that is excellent from the point of toxicity, environment and others, wherein reaction can be progressed effectively with Bronsted acid or Lewis acid catalyst. For example, the benzoylation reaction of alcohol can also be progressed easily, and further, the catalyst can be recovered and recycled easily. The para position of arylbis(perfluoroalkylsulfonyl)methane represented by the general formula [1] (wherein $R^1$ shows a substituted or unsubstituted aryl group, $Rf^1$ and $Rf^2$ are independent to each other and show a perfluoroalkyl group), a pentafluorophenylbis(perfluoroalkylsulfonyl)methane, for example, is supported on a polystyrene resin, and a polystyrene-supported arylbis(perfluoroalkylsulfonyl)methane represented by the general formula [3] (wherein $R^3$ shows a substituted or unsubstituted arylene group, $Rf^1$ and $Rf^2$ are the same as described above) is obtained.

(Chemical formula 1) [1]

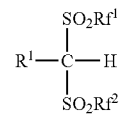

(Chemical formula 2) [3]

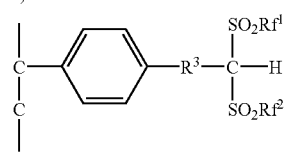

17 Claims, No Drawings

OTHER PUBLICATIONS

Ishihara et al, "Polystyrene-bound Tetrafluorophenylbis(triflyl)methane As An Organic-Solvent-Swellable And Strong Bronsted Acid Catalyst," Angewandte Chemie International Edition, vol. 40, No. 21, Nov. 5, 2001, pp. 4077-4079.

Ishihara et al, "Polystyrene-bound Tetrafluorophenylbis (triflyl)methane As An Organic-Solvent-Swellable And Strong Bronsted Acid Catalyst," Angewandte Chemie, vol. 113, No. 21, Nov. 5, 2001, pp. 4201-4203.

Ishihara et al, "Pyrolysis of benzenediazonium bis (trifluoromethanesulfonyl)methide" Journal of Fluorine Chemistry, vol. 106, pp. 139-141, 2000.

Zhu, Shizheng, "Synthesis and Reactions of Phenyliodonium Bis(perfluoroalkanesulfonyl) Methides," Heteroatom Chemistry, 1994, vol . 5, No. 1, pp. 9-18.

Zhu, Shizheng, "A new synthetic route to aryl bis (perfluoroalkanesulfonyl)methanes: structures of tolyldiazonium bis(trifluoromethanesulfonyl)methide and 4-nitrophenyl-hydrazono bis(trifluoromethanesulfonyl) methane," J. Fluorine Chem., 1993, vol. 64, pp. 47-60.

Liston, David J. et al., "Observations on Silver Salt Metathesis Reactions with Very Weakly Coordinating Anions," J. Am. Chem. Soc., 1989, vol. 111, pp. 6643-6648.

European Patent Office, Supplementary European Search Report for EP 02 70 2913, published Apr. 27, 2005.

* cited by examiner

POLYMER-SUPPORTED ARYLBIS(PERFLUOROALKYLSULFONYL)-METHANE

TECHNICAL FIELD

The present invention relates to an arylbis(perfluoroalkylsulfonyl)methane supported by a polymer such as polystyrene resin and the like, that is, a polymer-supported arylbis(perfluoroalkylsulfonyl)methane, a method for producing said compound, catalysts such as Bronsted acid catalyst and the like which comprises said compound as an active ingredient, and a method for synthesizing organic compounds by using said catalysts.

BACKGROUND ART

Trifluoromethane sulfonyl (—$SO_2CF_3$; triflyl, Tf) group is known as one of the strongest electron-accepting group, which has an action to increase the protonic acidity of its α position (J. Am. Chem. Soc. 96, 2275, 1974; Synthesis, 691, 1997; J. Fluorine Chem. 66, 301, 1994). For example, bis(triflyl)methane ($CH_2Tf_2$; $pK_a(H_2O)$=−1) (J. Am. Chem. Soc. 106, 1510, 1984) and phenylbis(triflyl)methane (PhCHTf$_2$; $pK_a$(MeCN)=7.83) (J. Org. Chem. 63, 7868, 1998) are strong acids that do not have the ability to oxidize. The inherent acidity ΔGacid (in gas condition) estimated by Koppel et al. is as follows (J. Am. Chem. Soc. 116, 3047, 1994): $MeSO_3H$ (315.0)<$CH_2Tf_2$ (310.5)<$PhCHTf_2$ (310.3)<TfOH (299.5)<$NHTf_2$ (291.8)<$CHTf_3$ (289.0). These volatile crystalline solids are known to serve as a reactant when preparing a cationic organometallic dihydrido by protonating an organometallic hydrido (J. Am. Chem. Soc. 106, 1510, 1984; J. Chem. Soc., Chem. Commun. 1675, 1987; Inorg. Chem. 27, 1593, 1988; Inorg. Chem. 27, 2473, 1988; Organometallics 9, 1290, 1990). Based on these facts, it is expected that the steric and electronic effects of the aromatic group in the arylbis(triflyl)methane such as phenylbis(triflyl)methane and the like mentioned above, have a great effect on its Bronsted acidity and the property of their organometallic complex.

Heretofore, two methods have been known as a method for synthesizing the phenylbis(triflyl)methane mentioned above (J. Org. Chem. 38, 3358, 1973; Heteroatom Chem. 5, 9, 1994; J. Fluorine Chem. 64, 47, 1993; J. Fluorine Chem. 106, 139, 2000). One of the methods is a method wherein benzyl magnesium chloride is reacted with triflyl fluoride to synthesize phenylbis(triflyl)methane (40% yield) (J. Org. Chem. 38, 3358, 1973), and the other method is a method wherein light response between iodobenzene bis(triflylmethide) and benzene is conducted (61% yield) (Heteroatom Chem. 5, 9, 1994). The former requires a triflyl fluoride gas (bp=−21° C.) which is difficult to obtain, as a triflyl source, and the latter requires an excessive amount of benzene, a reactant, as a solvent. Moreover, in the case of the latter, arylbis(triflyl)methane is not formed when light response is conducted with allene, which has an electron-accepting group such as fluorobenzene.

Meanwhile, a method for synthesizing benzyl triflone has been reported by Hendrickson et al. (J. Am. Chem. Soc. 96, 2275, 1974; Synthesis, 691, 1997; J. Fluorine Chem. 66, 301, 1994). However, there was a problem that arylmethyl triflone could not be synthesized at a high yield when the aromatic group is an electron-accepting group and is inactivated (Synthesis, 691, 1997).

In addition, Lewis acid catalyst is known to be the most widely used catalyst in the aspect of organic synthesis. This Lewis acid catalyst associates with a specific functional group of an organic compound, forms a complex, and can be made to conduct a particular response only. The one that accepts an electron pair from which it reacts with is referred to as Lewis acid. Organic compounds generally have a functional group, and the functional group is usually a Lewis base, which attracts mutually with Lewis acid. The Lewis acid catalyst designed in this manner forms a complex with the functional group of the organic compound, and leads directly to the desired reaction. Due to this point, Lewis acid catalyst is also compared to an artificial enzyme. However, the reactivity and selectivity of the conventional Lewis acid catalyst was not so high compared to when enzyme was used, and was not sufficient. Therefore, a Lewis acid catalyst that has an excellent selectivity and reactivity, further capable of reacting under warm condition, has a good recovery rate and can be recycled, has been required.

Heretofore, a Lewis acid catalyst comprised of a compound shown by a general formula $M[RfSO_2—N—SO_2Rf']_n$ or $M[RfSO_2—N—SO_2Rf']_n \cdot mH_2O$ (wherein Rf and Rf' represent a perfluoroalkyl group having 1 to 8 carbon atoms, M represents an element selected from alkaline metal, alkaline earth metal, transition metal, rare earth, aluminum, gallium, iridium, thallium, silicon, germanium, tin, lead, arsenic, antimony, bismuth, selenium and tellurium, n represents an integer of the same number as the valence of the corresponding metal, and m represents a natural number from 0.5 to 20) (Japanese Laid Open Patent Application No. 07-246338), and a Lewis acid catalyst shown by the following formula, (Chemical formula 1)

[wherein X represents —N(Tf$^1$)Tf$^2$ [wherein Tf$^1$ represents —$SO_2Rf^1$, Tf$^2$ represents —$SO_2Rf^2$ (wherein each of Rf$^1$ and Rf$^2$ independently represents a fluorine atom or a perfluoroalkyl group)], R$^1$ represents a substituted or unsubstituted cyclopentadienyl group, —OR$^3$ or —N(Tf$^3$)R$^4$, R$^2$ represents a substituted or unsubstituted cyclopentadienyl group, —OR$^5$ or —N(Tf$^4$)R$^6$ [wherein Tf$^3$ represents —$SO_2Rf^3$, Tf$^4$ represents —$SO_2Rf^4$ (wherein each of Rf$^3$ and Rf$^4$ independently represents a fluorine atom or a perfluoroalkyl group), each of R$^3$, R$^4$, R$^5$ and R$^6$ independently represents a lower alkyl group, or, R$^3$ and R$^5$, R$^3$ and R$^6$, R$^4$ and R$^5$ or R$^4$ and R$^6$ form together a bivalent group], M represents an element selected from alkaline earth metal, rare earth element, transition metal, boron, aluminum, gallium, indium, thallium, silicon, germanium, tin, lead, arsenic, antimony, bismuth, selenium or tellurium, n represents an integer of valence −2 of the corresponding M, and has at least one of —N(Tf$^1$)Tf$^2$, —N(Tf$^3$)R$^4$ or —N(Tf$^4$)R$^6$] (Japanese Laid Open Patent Application No. 09-57110), have been known as Lewis acid catalysts.

Aside from the examples mentioned above, there have been disclosures of highly active acid catalysts, including a highly active Lewis acid catalyst that can be used under the coexistence of water, comprising a metallic halide shown by a general formula $M^+(X_1^-)q$ (wherein M represents at least one metal selected from a group comprising elements from IIIA family to VB family of the periodic table, $X_1$ represents a halogen atom, and q represents an integer that is identical to the valence number of M) and a quaternary type anion exchange resin (Japanese Laid Open Patent Application No. 09-262479), and an acid catalyst comprising a metallic salt of tris(perfluoroalkylsulfonyl)methide shown by the following formula [(RfSO$_2$)$_3$C]$_n$M$_2$ (however, Rf represents a perfluoroalkyl group having one or more carbon atoms, M$_2$ represents an element selected from alkaline metal, alkaline earth metal, transition metal including rare earth, zinc, cadmium, aluminum, gallium, indium, thallium, silicon, germanium, tin, lead, arsenic, antimony, bismuth, selenium or tellurium. n represents an integer of the same number as the valence of M$_2$) (Japanese Laid Open Patent Application No. 2000-219692).

Nafion (DuPont) is known as a solid catalyst having a super strong acidity. However, although it shows excellent swelling ability to water, alcohol and the like, it does not swell much in an aprotic organic solvent, which is frequently used in an organic reaction. If a solid catalyst having a super strong acidity can be used as a catalyst in a swelling condition, then it can be said that the solid catalyst is an excellent solid catalyst that exceeds Nafion. Due to this point, a solid catalyst that shows excellent swelling ability to organic solvents (for example, aromatic-based solvent, halogen-based solvent, ether-based solvent and the like) has been required. The object of the present invention is to provide a polymer-supported arylbis(perfluoroalkylsulfonyl)methane that is useful as a solid catalyst, which can be used in almost any reaction that progress with Bronsted acid or Lewis acid catalyst, has a high recovery rate, can be recycled easily, has versatility, and is also environment-friendly in that it does not contain metal; a method for producing said compound; catalysts such as Bronsted acid catalyst and the like comprising said compound; and a method for synthesizing organic compounds by using said catalysts.

The present inventors conducted a keen study to elucidate the object mentioned above. Sodium trifluoromethane sulfinate (TfNa) and trifluoromethane sulfonic acid anhydride (Tf$_2$O) were used as an electrophilic reactant as a triflyl source to synthesize pentafluorophenylbis(triflyl)methane; said pentafluorophenylbis(triflyl)methane and LiOH.H$_2$O were reacted in a diethylether to synthesize lithium pentafluorophenylbis(triflyl)methide; said lithium pentafluorophenylbis(triflyl)methide and 4-bromopolystyrene resin were reacted in a mixed solvent of benzene and THF under the presence of butyl lithium, the phenyl anion of the polystyrene resin was subjected to nucleophilic substitution reaction specifically in the para position of the pentafluorophenylbis(triflyl)methane to obtain a polystyrene-supported pentafluorophenylbis(triflyl)methane. It was found out that said polystyrene-supported pentafluorophenylbis(triflyl)methane serves as an excellent acid catalyst for acylation reaction of alcohol, aldol reaction, allylation reaction and the like, as a Bronsted acid or a Lewis acid catalyst. Thus, the present invention had been completed.

DISCLOSURE OF THE INVENTION

The present invention relates to a polymer-supported arylbis(perfluoroalkylsulfonyl)methane wherein arylbis(perfluoroalkylsulfonyl)methane represented by general formula [1]

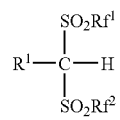

[1]

(wherein R$^1$ shows a substituted or unsubstituted aryl group, Rf$^1$ and Rf$^2$ are independent to each other and show a perfluoroalkyl group) is supported on an organic polymer resin (claim 1); the polymer-supported arylbis(perfluoroalkylsulfonyl)methane according to claim 1, wherein the organic polymer resin is a resin polymer capable of generating an anion with a basic reactant; the polymer-supported arylbis(perfluoroalkylsulfonyl)methane according to claim 1, wherein the resin polymer capable of generating an anion with a basic reactant is a resin polymer having a substituted or unsubstituted aryl group in its molecule; the polymer-supported arylbis(perfluoroalkylsulfonyl)methane according to claim 1, wherein the resin polymer having a substituted or unsubstituted aryl group in its molecule is a polystyrene resin; the polymer-supported arylbis(perfluoroalkylsulfonyl)methane according to claim 1, wherein the arylbis(perfluoroalkylsulfonyl)methane represented by the general formula [1] is supported on an organic polymer by a reaction of an electrophilic substituent of its aryl group with an anion of an organic polymer (claim 5); the polymer-supported arylbis(perfluoroalkylsulfonyl)methane according to claims 1 and 5, wherein the Rf$^1$ and Rf$^2$ in the general formula [1] are both a trifluoromethyl group (claim 6); the polymer-supported arylbis(perfluoroalkylsulfonyl)methane according to any of claims 1, 5–6, wherein the R$^1$ in the general formula [1] is a phenyl group, a naphthyl group, a 2,4,6-trimethylphenyl group, a 4-(trifluoromethyl)phenyl group, a 3,5-bis(trifluoromethyl)phenyl group, a pentafluorophenyl group or a perfluorobiphenyl group (claim 7); and the polymer-supported arylbis(perfluoroalkylsulfonyl)methane according to any of claims 1, 5–7, wherein the arylbis(perfluoroalkylsulfonyl)methane is a phenylbis(triflyl)methane, a 2-naphthylbis(triflyl)methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis(triflyl)methane, a pentafluorophenylbis(triflyl)methane or a {4-(pentafluorophenyl)-2,3,5,6-tetrafluorophenyl}bis(triflyl)methane (claim 8).

Further, the present invention relates to a method for producing a polymer-supported arylbis(perfluoroalkylsulfonyl)methane wherein said method is a method for producing the polymer-supported arylbis(perfluoroalkylsulfonyl)methane according to any of claims 1, 5–8, wherein a resin polymer capable of generating an anion with a basic reactant is reacted with a metallic salt of arylbis(perfluoroalkylsulfonyl)methane represented by general formula [2]

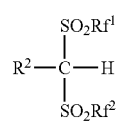

[2]

(wherein R$^2$ shows an aryl group having an electrophilic substituent, Rf$^1$ and Rf$^2$ are independent to each other and show a perfluoroalkyl group) (claim 6); the method for producing the polymer-supported arylbis(perfluoroalkylsulfonyl)methane according to claim 6, wherein a haloalkyl resin polymer is used as the resin polymer capable of generating an anion with a basic reactant (claim 7); the method for producing the polymer-supported arylbis(perfluoroalkylsulfonyl)methane according to claim 7, wherein a halogeno polystyrene resin is used as the haloalkyl resin polymer (claim 8); the method for producing the polymer-supported arylbis(perfluoroalkylsulfonyl)methane according to claim 8, wherein a 4-bromopolystyrene resin is used as the halogeno polystyrene resin (claim 9); the method for producing the polymer-supported arylbis(perfluoroalkylsulfonyl)methane according to any of claims 6 to 9, wherein the metallic salt of arylbis(perfluoroalkylsulfonyl)methane is any one of the metallic salts selected from alkaline metallic element, alkaline earth metallic element, transition metallic element, boron, silicon, aluminum, tin, zinc or bismuth (claim 10); the method for producing the polymer-supported arylbis(perfluoroalkylsulfonyl)methane according to claim 13, wherein the transition metallic element is any one of the metallic elements selected from scandium, yttrium, lanthanoid, copper, silver, titanium, zirconium or hafnium (claim 11); the method for producing the polymer-supported arylbis(perfluoroaklylsulfonyl)methane according to any of claims 6 to 11, wherein the metallic salt of arylbis(perfluoroalkylsulfonyl)methane is a lithium salt of pentafluorobis(trifluoromethylsulfone) (claim 12); the method for producing the polymer-supported arylbis(perfluoroalkylsulfonyl)methane according to any of claims 6 to 12, wherein a butyl lithium is used as the basic reactant (claim 13); the method for producing the polymer-supported arylbis(perfluoroalkylsulfonyl)methane according to any of claims 6 to 13, wherein a mixture of benzene and tetrahydrofuran is used as the solvent (claim 14).

The present invention also relates to a catalyst wherein the metallic salt of polymer-supported arylbis(perfluoroalkylsulfonyl)methane according to claim 1 is used as an active ingredient; a catalyst, wherein the catalyst is a Bronsted acid catalyst; a method for synthesizing an organic compound wherein the method is a method for synthesizing an organic compound by using the catalyst, wherein a catalytic reaction is conducted in a solvent under the presence of said catalyst claim 15; and the method for synthesizing the organic compound according to claim 16, wherein the catalytic reaction is an acetalyzation reaction, an acylation reaction of alcohol, an aldol-type reaction, an allylation reaction, a Diels-Alder reaction, a Friedel-Crafts reaction, a Mannich reaction, a glycosilation reaction, an esterification reaction, an ene reaction or a cationic polymerization reaction (claim 16).

BEST MODE OF CARRYING OUT THE INVENTION

There is no particular limitation to the polymer-supported arylbis(perfluoroalkylsulfonyl)methane of the present invention, as long as the arylbis(perfluoroalkylsulfonyl)methane represented by the general formula [1] (wherein $R^1$ shows a substituted or unsubstituted aryl group, $Rf^1$ and $Rf^2$ are independent to each other and show a perfluoroalkyl group) is chemically and/or physically supported on an organic polymer resin. However, an arylbis(perfluoroalkylsulfonyl)methane that is chemically supported on a resin polymer capable of generating an anion with a basic reactant, for example, the one that is chemically supported by the reaction of an electrophilic substituent of an aryl group of arylbis(perfluoroalkylsulfonyl)methane and an anion of an organic polymer is preferable. Examples of the resin polymer capable of generating an anion with a basic reactant include a resin polymer having a substituted or unsubstituted aryl group in its molecule and a resin polymer having a hydroxyl group in its molecule. More specifically, resin polymers that are supported on a polystyrene that is supported with poly(p-hydroxystyrene) and polyethylene glycol (product name: TENTAGEL) and the like, can be exemplified. The polymer resin of the polystyrene resin and the like as a carrier to support these arylbis(perfluoroalkylsulfonyl)methane, may be a homopolymer or a copolymer.

Further, in the case where the arylbis(perfluoroalkylsulfonyl)methane represented by the general formula [1] is a pentafluorophenylbis(perfluoroalkylsulfonyl)methane, the one that is supported on an organic polymer resin at its para position is advantageous, and in the case where said arylbis(perfluoroalkylsulfonyl)methane represented by the general formula [1] is a {4-(pentafluorophenyl)-2,3,5,6-tetrafluorophenyl}bis(triflyl)methane, the one that is supported on an organic polymer resin at its 4' position is advantageous, in that synthesis can be conducted easily. Moreover, as the arylbis(perfluoroalkylsulfonyl)methane wherein the arylbis(perfluoroalkylsulfonyl)methane represented by the general formula [1] is supported on a polystyrene resin, a polystyrene-supported arylbis(perfluoroalkylsulfonyl)methane represented by general formula [3] can be exemplified.

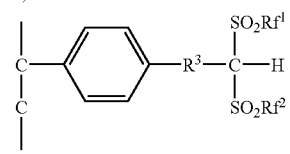

(Chemical formula 4)

[3]

(wherein $R^3$ is a substituted or unsubstituted allylene group, $Rf^1$ and $Rf^2$ are independent to each other and show a perfluoroalkyl group).

The $Rf^1$ and $Rf^2$ in the general formulae [1] and [3] mentioned above show a perfluoroalkyl group that may be the same or different from each other, preferably a C1–C8 perfluoroalkyl group such as trifluoromethyl group and the like. Specific examples of —$SO_2Rf^1$ and —$SO_2Rf^2$ containing these $Rf^1$ and $Rf^2$ include a trifluoromethylsulfonyl group, a perfluoroethylsulfonyl group, a perfluoropropylsulfonyl group, a perfluoroisopropylsulfonyl group, a perfluorobutylsulfonyl group, a perfluoroisobutylsulfonyl group, a perfluoropentylsulfonyl group, a perfluoroisopentylsulfonyl group and a perfluoroneopentylsulfonyl group.

Examples of $R^1$ in the general formula [1] mentioned above include an aryl group such as a substituted or unsubstututed phenyl group, naphthyl group, biphenyl group and the like. Moreover, examples of $R^3$ in the formula [3] mentioned above include an allylene group such as a substituted or unsubstituted phenylene group, naphthylene group, biphenylene group and the like. Examples of the substituent for these cases include a C1–C4 lower alkyl group such as methyl group and the like, a halogenated C1–C4 lower alkyl group such as trifluoromethyl group and the like, a halogen atom such as fluorine and the like, an alkoxy group, a sulfonyl group and an amino group. Specific examples of said $R^1$ include a phenyl group, a naphthyl group, a 2,4,6-trimethylphenyl group, a 4-(trifluoromethyl)phenyl group, a 3,5-bis(trifluoromethyl)phenyl group, a pentafluorophenyl group, a p-tolyl group, an m-tolyl group, a mesityl group, a xylyl group, a biphenyl group, a perfluorobiphenyl group, a p-chlorophenyl group, and an o-chlorophenyl group.

Specific examples of the arylbis(perfluoroalkylsulfonyl) methane in the polymer-supported arylbis(perfluoroalkylsulfonyl)methane such as polystyrene resin and the like of the present invention include a phenylbis(triflyl)methane, a 2-naphthylbis(triflyl)methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis(triflyl)methane, a pentafluorophenylbis(triflyl)methane and a {4-(pentafluorophenyl)-2,3,5,6-tetrafluorophenyl}bis(triflyl)methane.

There is no particular limitation to the method for producing the polymer-supported arylbis(perfluoroalkylsulfonyl)methane of the present invention, as long as it is a method wherein a resin polymer capable of generating an anion with a basic reactant, for example, a haloalkyl resin polymer, is reacted with a metallic salt of arylbis(perfluoroalkylsulfonyl)methane represented by the aforementioned general formula [2] (wherein $R^2$ shows an aryl group having an electrophilic substituent, $Rf^1$ and $Rf^2$ are independent to each other and show a perfluoroalkyl group). By the nucleophilic substitution reaction of the metallic salt of arylbis(perfluoroalkylsulfonyl)methane, the electrophilic substituent of the metallic salt of arylbis(perfluoroalkylsulfonyl)methane is reacted with an anion in the resin polymer molecule, and the polymer-supported arylbis(perfluoroalkylsulfonyl)methane of the present invention can be produced. The $R^2$ in the general formula [2] shows an aryl group such as a phenyl group having an electrophilic substituent (electron-accepting group) such as $-+NH_3$, $-CF_3$, $-CCl_3$, $-NO_2$, $-CN$, $-CHO$, $-COCH_3$, $-COOC_2H_5$, $-COOH$, $-SO_2CH_3$, $-SO_3$ and the like, a naphthyl group, a biphenyl group and the like. As is the case with the aforementioned, $Rf^1$ and $Rf^2$ are independent to each other and show a perfluoroalkyl group. Further, as the haloalkyl resin polymer mentioned above, a resin polymer having a substituted or unsubstituted aryl group in its molecule and the like can be given as an example, and among them, a halogenopolystyrene resin such as a 4-bromopolystyrene resin and the like can be preferably exemplified. Particularly, when a 4-bromopolystyrene resin, and a pentafluorophenylbis(perfluoroalkylsulfonyl)methane or a {4-(pentafluorophenyl)-2,3,5,6-tetrafluorophenyl}bis(triflyl)methane are used, the supporting can be conducted with one step of reaction. These resin polymers may be a homopolymer or a copolymer. As a copolymer, for example, one having a crosslinking structure of a copolymer of styrene and divinylbenzyl can be preferably exemplified.

Examples of the metallic salt of arylbis(perfluoroalkylsulfonyl)methane mentioned above include metallic salts wherein the element composing the metallic salt is an alkaline metallic element (lithium, sodium, potassium, rubidium, cesium, francium and the like), an alkaline earth metallic element (beryllium, magnesium, calcium, strontium, barium, radium and the like), a transition metallic element (scandium, yttrium, lanthanoid, cerium, praseodymium, neodymium, promethium, samarium, europium, gadolinium, terbium, dysprosium, holmium, erbium, thulium, ytterbium, lutetium, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, boron, aluminum, platinum, copper, silver, gold, zinc, cadmium, mercury and the like), a boron, a silicon, an aluminum, a tin, a zinc, a bismuth and the like. Among these, a lithium salt of pentafluorophenylbis(trifluoromethylsulfonyl)methane, that is, a lithium pentafluorophenylbis(trifluoromethyl sulfonyl)methide, or a lithium salt of {4-(pentafluorophenyl)-2,3,5,6-tetrafluorophenyl}bis(triflyl)methane, that is, a lithium{4-(pentafluorophenyl)-2,3,5,6-tetrafluorophenyl}bis(triflyl)methide can particularly and preferably be exemplified.

In order to produce such metallic salt of arylbis(perfluoroalkylsulfonyl)methane supported on a polystyrene resin, for example, the arylbis(perfluoroalkylsulfonyl)methane represented by the general formula [1] mentioned above can be subjected to (1) neutralization reaction with a hydroxide of a metal, (2) reaction by heating under reflux with a salt or an oxide of a transition metal, and (3) reaction with a silver carbonate under shade. Further, another method for production, which is the exchange reaction of metal species, wherein the metallic salt such as silver salt and the like of the arylbis(perfluoroalkylsulfonyl)methane represented by the general formula [1], and a halide of a metal of different metal species are reacted, can be exemplified. Specific examples of the hydroxide of the metal in the neutralization reaction in (1) mentioned above include the hydroxide of alkaline metal such as lithium hydroxide, sodium hydroxide and potassium hydroxide, and the hydroxide of alkaline earth metal such as calcium hydroxide. A method in which a solution wherein the hydroxides of said metals are dissolved in a solvent such as diethylether and the like is used to react for 10 minutes to over 10 hours, can be exemplified. Specific examples of the salt or the oxide of the transition metal in the reaction by heating under reflux in (2) mentioned above include a lanthanoid metallic salt such as chloride of lanthanum and cerium, and a scandium oxide such as $Sc_2O_3$ and the like. A method wherein heating under reflux in an aqueous solution is conducted for 10 minutes to over 10 hours can be exemplified.

A specific example of the arylbis(perfluoroalkylsulfonyl) methane represented by the general formula [1] mentioned above include an arylbis(perfluoroalkylsulfonyl)methane such as a phenylbis(triflyl)methane, a 2-naphthylbis(triflyl) methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis(triflyl) methane, a pentafluorophenylbis(triflyl)methane, a {4-(pentafluorophenyl)-2,3,5,6-tetrafluorophenyl}bis(triflyl) methane and the like. However, the examples are not limited to these. Moreover, it is preferable to use a {4-(pentafluorophenyl)-2,3,5,6-tetrafluorophenyl}bis(triflyl)methane or a pentafluorophenylbis(triflyl)methane, since they are organic acids that are stronger than TfOH.

Further, as to the method for producing the arylbis(perfluoroalkylsulfonyl)methane represented by the general formula [1] mentioned above, there is no particular limitation as long as it is a method wherein an aryl halomethane is reacted with a perfluoroalkyl sulfinate; the arylmethylperfluoroalkylsulfone produced is reacted with a deprotonation agent comprised of an organic metal or a metallic salt; and the metallic salt of arylmethylperfluoroalkylsulfone obtained is reacted with an anhydrous perfluoroalkyl sufonic acid. There is no particular limitation to the aryl halomethane used in this method for production as long as it is a methane that is substituted by a substituted or unsubstituted aryl group and a halogen atom. Specifically, examples include a benzyl bromide, a 2-bromomethylnaphthalene, a 1-chloromethylnaphthalene, a 2,4,6-trimethylphenylmethylchloride, a 4-(trifluoromethyl)phenylmethylbromide, a 3,5-bis(trifluoromethyl)phenylmethylbromide, a pentafluorophenylmethylbromide and a 4-(bromomethyl)perfluorobiphenyl(perfluorobiphenylmethylbromide).

A preferable example of the perfluoroalkyl sulfinate used in the method for producing the arylbis(perfluoroalkylsulfonyl)methane represented by the general formula [1] mentioned above is a metallic salt of a C1–C8 perfluoroalkyl sulfinic acid including, for example, a trifluoromethyl sulfinic acid, a perfluoroethyl sulfinic acid, a perfluoropropyl sulfinic acid, a perfluoroisopropyl sulfinic acid, a perfluorobutyl sulfinic acid, a perfluoroisobutyl sulfinic acid, a perfluoropentyl sulfinic acid, a perfluoroisopentyl sulfinic acid and a perfluoroneopentyl sulfinic acid. An alkaline metallic salt and an alkaline earth metallic salt can be exemplified as the metallic salt, however, the alkaline metallic salt such as sodium and the like is preferable.

It is preferable for the nucleophilic substitution reaction of the aryl halomethane and the perfluoroalkyl sulfinate in the method for producing the arylbis(perfluoroalkylsulfonyl)methane represented by the general formula [1] mentioned above to be conducted in a condition wherein an arylmethylperfluoroalkylsulfone can be synthesized at a high efficiency, for example, by heating under reflux using a solvent with or without the presence of a catalyst. It is preferable for the molarity of the aryl halomethane in the reaction system mentioned above to be 0.2 to 0.4 M, and for the perfluoroalkyl sulfinate such as sodium trifluoromethane sulfinate to be used 1.0 to 1.5 equivalent weight, especially about 1.3 equivalent weight, to the aryl halomethane. In addition, when a catalyst is used, the use of a catalyst comprising an iodide such as tetrabutyl ammonium iodide, potassium iodide and the like is preferable. The amount of these catalysts to be used is, for example, 2 to 20 mol %, preferably 5 to 10 mol % to the aryl halomethane. Further, acetonitrile, propionitrile, nitromethane, nitropropane and the like can be given as examples of the solvent, however, it is preferable to use propionitrile in view of the applicabiliity of the polarity and boiling point. The reaction mentioned above is preferable to be conducted by heating under reflux in a dry inert gas atmosphere, such as in an argon or nitrogen atmosphere. It is preferable for the reaction to be conducted by heating under reflux at 80 to 150° C., preferably 100 to 120° C. for 12 to 48 hours. Examples of the methods for purifying the arylmethyl triflone obtained by these synthesis reactions are, for example, a method wherein the reactant solution obtained by reacting under the condition mentioned above is filtrated to remove salt, followed by a silica gel column chromatography using hexane and ethyl acetate (EtOAc) as a developing solvent, and a recrystallization operation using hexane and toluene, or the like.

Next, the arylbis(perfluoroalkylsulfonyl)methane represented by the general formula [1] can be produced by the reaction of an arylmethylperfluoroalkylsulfone produced by the nucleophilic substitution reaction of aryl halomethane and perfluoroalkyl sulfinate with a deprotonation agent comprising an organic metal or a metallic salt, followed by the reaction of the metallic salt of arylmethylperfluoroalkylsulfone obtained with a perfluoroalkyl sulfonic acid anhydride. However, there is no particular limitation to the deprotonation agent mentioned above, as long as it is an organic metal or a basic reactant having a deprotonating action. An alkaline metallic salt and alkaline earth metallic salt of lower alkyl, more specifically, t-BuLi and t-BuMgCl can preferably be exemplified. Further, a preferable example of the perfluoroalkyl sulfonic acid anhydride mentioned above is a C1–C8 perfluoroalkyl sulfonic acid anhydride including a trifluoromethane sulfonic acid anhydride (Tf$_2$O), a perfluoroethane sulfonic acid anhydride, a perfluoropropane sulfonic acid anhydride, a perfluoroisopropane sulfonic acid anhydride, a perfluorobutane sulfonic acid anhydride, a perfluoroisobutane sulfonic acid anhydride, a perfluoropentane sulfonic acid anhydride, a perfluoroisopentane sulfonic acid anhydride and a perfluoroneopentane sulfonic acid anhydride. Among these, Tf$_2$O is especially preferable. There is no particular limitation to the method wherein the arylmethylperfluoroalkylsulfone mentioned above is reacted with a deprotonation agent such as alkyl lithium, alkyl magnesium chloride and the like and a perfluoroalkyl sulfonic acid anhydride such as Tf$_2$O and the like, as long as it is a method which can produce arylbis(perfluoroalkylsulfonyl)methane such as arylbis(trifluoromethylsulfonyl)methane and the like at a high yield. Specific examples include, for example: a method wherein an arylmethylperfluoroalkylsulfone such as arylmethyl triflone and the like is dissolved in a solvent such as a diethylether and the like, alkyl lithium and the like is added at −78° C., the solvent is reacted for 5 to 10 minutes, then Tf$_2$O is added after the reaction to react for 1 to 2 hours at room temperature; and a method wherein alkyl magnesium chloride is added at −78° C. to react for 30 minutes, then reacted at 0° C. for 30 minutes, and Tf$_2$O is added at −78° C. after the reaction to react for 1 to 2 hours at room temperature, and the like. However, it is preferable to repeat said operation multiple times, in view of the increase in yield.

Further, in order to obtain an arylbis(perfluoroalkylsulfonyl)methane such as arylbis(trifluoromethylsulfonyl)methane at a high yield, it is preferable to react 1.7 to 2.4 equivalent weight of an organic metal such as alkyl lithium and the like or 1.0 to 1.2 equivalent weight of a perfluoroalkyl sulfonic acid anhydride such as Tf$_2$O and the like with the arylmethylperfluoroalkylsulfone such as arylmethyl triflone and the like. For example, in the case where t-BuLi (1.2 equivalent weight) is used for a benzyl triflone, since phenylbis(triflyl)methane is a much more stronger acid compared to the benzyl triflone, the phenylbis(triflyl)methane produced is immediately deprotonated by the lithium salt of the benzyl triflone, the phenylbis(triflyl)methane becomes a lithium salt, the lithium salt of the phenylbis(triflyl)methane obtained is converted to a phenyltris(triflyl)methane by the reaction with Tf$_2$O, the molar ratio of the benzyl triflone and the phenyltris(triflyl)methane becomes approximately 1:1, and only a little amount of the phenylbis(triflyl)methane is synthesized. However, in the case where 2.2 equivalent weight of t-BuLi is used for the benzyl triflone, the phenylbis(triflyl)methane produced is deprotonated by t-BuLi, and the benzyl triflone is quantitatively converted to a lithium salt of phenylbis(triflyl)methane. However, in the case where a pentafluorophenylbis(triflyl)methane is produced by using a pentafluoromethylbromide, a pentafluorophenylbis(triflyl)methane and a 4-tert-butyl-2,3,5,6-tetrafluorophenylbis(triflyl)methane are both obtained at a ratio of 1:1 (45% yield, respectively). Therefore, in this case, using 1.0 equivalent weight of t-BuLi and 0.5 equivalent weight of Tf$_2$O completely suppresses the production of 4-tert-butyl-2,3,5,6-tetrafluorophenylbis(triflyl)methane, and a pentafluorophenylbis(triflyl)methane with Tf$_2$O as a base can be obtained at a high yield.

As to the reaction of a resin polymer with a metallic salt of arylbis(perfluoroalkylsulfonyl)methane in the method for producing the polymer-supported arylbis(perfluoroalkylsulfonyl)methane of the present invention, the polymer-supported arylbis(perfluoroalkylsulfonyl)methane can be obtained by the following example: a resin polymer is swelled in a solvent such as toluene, benzene or the like, a basic reactant is added therein under an inert gas atmosphere and is heated to a range of 20 to 80° C., preferably 60° C. After stirring the solvent, it is returned to room temperature, and a reactant solvent is added to a resin wherein the solution part is removed, then once cooled to a range of −10 to 25° C., preferably 0° C., a metallic salt of arylbis(perfluoroalkylsulfonyl)methane is added to the solvent and stirred at room temperature, then heated to a range of 25 to 85° C., preferably 70° C., the arylbis(perfluoroalkylsulfonyl)methane is supported on a resin polymer, then cooled, washed and dried. There is no particular limitation to the basic reactant mentioned above, as long as it is capable of generating an anion on a resin polymer, however, an alkyl lithium such as butyl lithium and the like is preferable. As the reactant solvent, a mixed solution of benzene and tetrahydrofuran is preferable in terms of the reaction yield. Unlike toluene, benzene does not react with the butyl lithium and the like mentioned above, and its yield does not decrease.

Any catalyst can be used as the catalyst of the present invention, as long as it is a solid acid catalyst that contains the polymer-supported arylbis(perfluoroalkylsulfonyl)methane of the present invention mentioned above as an active ingredient. For example, a Bronsted acid catalyst comprising the polystyrene-supported arylbis(perfluoroalkylsulfonyl)methane represented by the general formula [2] mentioned above, can be preferably exemplified. The catalyst of the present invention can be easily recovered and recycled, and can be easily produced as well. Therefore, it can be said that the catalyst is very practical. The solid acid catalyst of the present invention can be used advantageously in acylation reaction of alcohol, Mukaiyama aldol reaction, Hosomi-Sakurai allylation reaction, acetalyzation reaction of ketone and the like. Particularly, in the acylation reaction of alcohol with the use of a Bronsted acid catalyst comprising the polystyrene-supported arylbis(perfluoroalkylsulfonyl)methane represented by the general formula [2] mentioned above or the like, acetylation as well as benzoylation, which has a low reactivity, can be easily progressed. Among the polymer-supported Bronsted acid, so far, there is hardly anything known except Nafion (DuPont) as the one having a strong acidic proton that can serve as an acid catalyst. However, as the reaction did not progress at all when benzoylation mentioned above was tested with the use of said Nafion as a catalyst, it is clear that the catalyst of the present invention is advantageous.

As described above, organic compounds such as pharmaceuticals, agricultural chemicals, asymmetric catalysts, various types of functional materials and the like, can be synthesized by using as a catalyst a polymer-supported arylbis(perfluoroalkylsulfonyl)methane such as the polystyrene-supported arylbis(perfluoroalkylsulfonyl)methane of the present invention or the like. A specific example of said method for synthesizing is a method wherein a catalytic reaction is conducted under the presence of a catalyst which comprises the polymer-supported arylbis(perfluoroalkylsulfonyl)methane mentioned above as an active ingredient, in an aqueous solution, in an organic solvent or in a mixed solvent of water and organic solvent. Specific examples of the catalytic reaction mentioned above include the aforementioned acylation reaction of alcohol (acetylation, benzoylation reaction), an aldol-type reaction, an allylation reaction, an acetalyzation reaction, as well as a Diels-Alder reaction, a Friedel-Crafts reaction, a Mannich reaction, a glycosilation reaction, an esterification reaction, an ene reaction, a cationic polymerization reaction, an interesterification reaction, a Mannich-type reaction, a Michael addition reaction, a conjugate addition reaction, a dehydration reaction, a dehydration/condensation reaction and a polymerization reaction.

The present invention will now be explained further in more details with the examples below, however, the scope of the invention is not limited to the exemplifications.

EXAMPLE 1

Analysis and Material

The infrared radiation spectrum was determined by using a Shimadzu FTIR-9100. The $^1$H NMR spectrum was determined by using a Varian Gemini-300 (300 MHz) nuclear magnetic resonance apparatus. The chemical shift of $^1$H NMR was indicated by ppm wherein a solvent as an internal standard (tetramethylsilane at 0 ppm) was used. The division pattern was shown as singlet: s, doublet: d, triplet: t, quartet: q, multiplet: m and broad peak: br. The $^{13}$C NMR spectrum was determined by using a Varian Gemini-300 (125 MHz) nuclear magnetic resonance apparatus, and was indicated by ppm wherein a solvent as an internal standard ($CDCl_3$ at 77.0 ppm) was used. The $^{19}$F NMR spectrum was determined by using a Varian Gemini-300 (282 MHz) nuclear magnetic resonance apparatus, and was indicated by ppm wherein a solvent as an internal standard ($CF_3C_6H_5$ at −64.0 ppm) was used. High-performance liquid chromatography (HPLC) analysis was conducted with a Shimadzu LC-10AD instrument and an SPD-M10A UV detector by using a chiral column (Daicel, AS or OD-H). All of the following examples were conducted in a glass instrument dried in an oven, by using a magnetic stirrer. The reaction product was purified on a Silica Gel E. Merck 9385 or a Silica Gel 60 Extra Pure by flash chromatography.

EXAMPLE 2

Synthesis of Arylmethyl Triflone

Each of the mixed solutions of aryl halomethyl (10 mmol), sodium trifluoromethane sulfinate (2.0 g: 13 mmol), propionitrile (30 mL) and tetrabutyl ammonium iodide (0.37 g: 1 mmol), shown in Table 1, were subjected to heating under reflux in an argon atmosphere for approximately 1 day. After the heating under reflux, the reaction solutions were cooled to room temperature, and were concentrated after removing the salt by filtration. The crude products obtained were purified by silica gel column chromatography (developing solvent: hexane-EtOAc) or recrystallization operation (hexane-toluene) to obtain arylmethyl triflone. The yield of each of the arylmethyl triflone is indicated in Table 1, and the physical property of each of the arylmethyl triflone is shown below. Table 1 showed that when sodium trifluoromethane sulfinate (TfNa) was used as an electrophilic reactant as a triflyl source, and heating under reflux with aryl halomethane was conducted by using propionitrile as a solvent under the presence of a tetrabutyl ammonium iodide catalyst, arylmethyl triflone can be obtained at a high yield than the method of Hendrickson et al. (Synthesis, 691, 1997). Table 1 also showed that pentafluorophenylmethyl triflone was obtained at a yield of 89%.

TABLE 1

| aryl halomethane | arylmethyl triflone | [yield (%)] |
|---|---|---|
| $PhCH_2Br$ | $PhCH_2Tf$ | 94 |
| 2-$NaphCH_2Br$ | 2-$NaphCH_2Tf$ | >99 |

TABLE 1-continued

| aryl halomethane | arylmethyl triflone | [yield (%)] |
|---|---|---|
| 1-NaphCH$_2$Cl | 1-NaphCH$_2$Tf | 99 |
| 2,4,6-Me$_3$C$_6$H$_2$CH$_2$Cl | 2,4,6-Me$_3$C$_6$H$_2$CH$_2$Tf | 90 |
| 4-CF$_3$C$_6$H$_4$CH$_2$Br | 4-CF$_3$C$_6$H$_4$CH$_2$Tf | >99 |
| 3,5-(CF$_3$)$_2$C$_6$H$_3$CH$_2$Br | 3,5-(CF$_3$)$_2$C$_6$H$_3$CH$_2$Tf | 76 |
| C$_6$F$_5$CH$_2$Br | C$_6$F$_5$CH$_2$Tf | 89 |

Benzyl triflone (2-Benzyl Triflone; J. Fluorine Chem. 66, 301, 1994): IR (KBr) 1362, 1347, 1223, 1198, 1188, 1125, 776, 698, 640, 525, 507 cm$^{-1}$; $^1$H NMR (CDCl$_3$, 300 MHz) δ 4.48 (s, 2H), 7.42–7.47 (m, 5H); $^{19}$F NMR (CDCl$_3$, 282 MHz) δ−77.6 (s, 3F, CF$_3$).

2-naphthylmethyl triflone (2-Naphthylmethyl Triflone): IR (KBr) 1358, 1345, 1221, 1194, 1125, 831, 756, 658, 608, 486 cm$^{-1}$; $^1$H NMR (CDCl$_3$, 300 MHz) δ 4.65 (s, 2H), 7.50 (dd, J=1.8, 8.4 Hz, 1H), 7.54–7.58 (m, 2H), 7.86–7.94 (m, 4H); $^{13}$C NMR (CDCl$_3$, 125 MHz) δ 56.3, 119.8 (q, J$_{CF}$=326 Hz, 1C), 120.3, 126.9, 127.4, 127.5, 127.8, 128.1, 129.2, 131.5, 133.1, 133.6; $^{19}$F NMR (CDCl$_3$, 282 MHz) δ−77.6 (s, 3F, CF$_3$). Anal. Calcd for C$_{12}$H$_9$O$_2$F$_3$S: C, 52.55; H, 3.31; F, 20.78; S, 11.69. Found C, 52.51; H, 3.33; F, 20.81; S, 11.65.

1-naphthylmethyl triflone (1-Naphthylmethyl Triflone): IR (KBr) 1510, 1358, 1223, 1200, 804, 776, 658, 486 cm$^{-1}$; $^1$H NMR (CDCl$_3$, 300 MHz) δ 4.99 (s, 2H), 7.53 (dd, J=7.8, 8.4 Hz, 1H), 7.62 (d, J=7.8 Hz, 1H), 7.58 (ddd, J=0.9, 6.9, 8.3 Hz, 1H), 7.65 (ddd, J=1.5, 6.9, 8.4 Hz, 1H), 7.93 (dd, J=1.5, 8.3 Hz, 1H), 7.98 (dd, J=8.4 Hz, 1H), 8.04 (dd, J=0.9, 8.4 Hz, 1H); $^{13}$C NMR (CDCl$_3$, 125 MHz) δ 53.0, 119.2, 120.0 (q, J$_{CF}$=326 Hz, 1C), 123.3, 125.3, 126.5, 127.5, 129.0, 131.1, 131.5, 132.3, 134.0; $^{19}$F NMR (CDCl$_3$, 282 MHz) δ−78.1 (s, 3F, CF$_3$). Anal. Calcd for C$_{12}$H$_9$O$_2$F$_3$S: C, 52.55; H, 3.31; F, 20.78; S, 11.69. Found C, 52.53; H, 3.29; F, 20.75; S, 11.73.

2,4,6-trimethylphenylmethyl triflone (2,4,6-Trimethylphenylmethyl Triflone): IR (KBr) 1358, 1206, 1117, 864, 619, 550, 500, 469 cm$^{-1}$; $^1$H NMR (CDCl$_3$, 300 MHz) δ 2.29 (s, 3H), 2.43 (s, 6H) 4.62 (s, 2H), 6.96 (s, 2H); $^{13}$C NMR (CDCl$_3$, 125 MHz) δ 20.3, 21.0 (2C), 49.8, 117.0, 120.0 (q, J$_{CF}$=326 Hz, 1C, CF$_3$), 129.9 (2C), 139.7 (2C), 139.8; $^{19}$F NMR (CDCl$_3$, 282 MHz) δ−79.7 (s, 3F, CF$_3$). Anal. Calcd for C$_{11}$H$_{13}$O$_2$F$_3$S: C, 49.62; H, 4.92; F, 21.40; S, 12.04. Found C, 49.58; H, 4.53; F, 21.35; S, 12.06.

4-(trifluoromethyl)phenylmethyl triflone (4-(Trifluoromethyl)phenylmethyl Triflone; Synthesis, 691, 1997): IR (KBr) 1356, 1341, 1227, 1210, 1144, 1121, 855, 658, 513 cm$^{-1}$; $^1$H NMR (CDCl$_3$, 300 MHz) δ 4.53 (s, 2H), 7.58 (d, J=8.0 Hz, 2H), 7.72 (d, J=8.0 Hz, 2H); $^{19}$F NMR (CDCl$_3$, 282 MHz) δ −77.5 (s, 3F, CF$_3$), −64.3 (s, 3F, CF$_3$).

3,5-bis(trifluoromethyl)phenylmethyl triflone (3,5-Bis(trifluoromethyl)phenylmethyl Triflone): IR (KBr) 1376, 1362, 1277, 1175, 1117, 918, 910, 669 cm$^{-1}$; $^1$H NMR (CDCl$_3$, 300 MHz) δ 4.60 (s, 2H), 7.91 (s, 2H), 8.01 (s, 1H); $^{13}$C NMR (CDCl$_3$, 125 MHz) δ 55.0, 119.6 (q, J$_{CF}$=326 Hz, 1C, CF$_3$), 122.6 (q, J$_{CF}$=272 Hz, 2C, 2CF$_3$), 124.2 (septet, J$_{CF}$=4 Hz, 1C), 126.1, 131.3 (2C), 132.9 (q, J$_{CF}$=34 Hz, 2C); $^{19}$F NMR (CDCl$_3$, 282 MHz) δ−77.4 (s, 3F, CF$_3$), −64.3 (s, 6F, 2CF$_3$). Anal. Calcd for C$_{10}$H$_3$O$_2$F$_9$S: C, 33.53; H, 0.84; F, 47.74; S, 8.95. Found C, 33.48; H, 0.91; F, 47.87; S, 8.89.

Pentafluorophenylmethyl triflone (Pentafluorophenylmethyl Triflone): IR (KBr) 1509, 1374, 1210, 1121, 995 cm$^{-1}$; $^1$H NMR (CDCl$_3$, 300 MHz) δ 4.64; $^{13}$C NMR (CDCl$_3$, 125 MHz) δ 44.3, 100.0 (dt, J$_{CF}$=4, 17 Hz, 1C, ipso-C), 119.5 (q, J$_{CF}$=326 Hz, 1C, CF$_3$), 137.9 (d, J$_{CF}$=251 Hz, 2C, 2m-C), 142.8 (d, J$_{CF}$=258 Hz, 1C, p-C), 145.9 (d, J$_{CF}$=252 Hz, 2C, 2o-C); $^{19}$F NMR (CDCl$_3$, 282 MHz) δ−160.0 (d, J=15.2 Hz, 2F, 2m-F), 149.0 (s, 1F, p-F), 139.4 (d, J=15.2 Hz, 2F, 2o-F), −78.3 (s, 3F, CF$_3$). Anal. Calcd for C$_8$H$_2$O$_2$F$_8$S: C, 30.59; H, 0.64; F, 48.38; S, 10.21. Found C, 30.49; H, 0.73; F, 48.37; S, 10.18.

EXAMPLE 3

Synthesis of Arylbis(triflyl)methane

Each of the arylmethyl triflone (0.5 mmol) obtained from Example 2 were dissolved in diethylether (3 mL), and their solutions were prepared, respectively. These solutions were cooled to −78° C., then added with 1.1 equivalent weight (0.55 mmol) of t-BuLi (0.34 mL, 1.6 M pentane solution), and were stirred for 10 minutes. Next, Tf$_2$O (46 μL, 0.275 mmol) was added, the temperature of the reaction solution was raised to room temperature, and the solution was further stirred for 1 hour. After cooling the solution again to −78° C., 1.1 equivalent weight (0.55 mmol) of t-BuLi (0.34 mL, 1.6 M pentane solution) was added, and the solution was stirred for 10 minutes. Subsequently, Tf$_2$O (46 μL, 0.275 mmol) was added, the temperature of the reaction solution was raised to room temperature, and the solution was further stirred for 1 hour. Then, water was added to stop the reaction, the solution was neutralized, and then washed with hexane. These aqueous phases were acidified with 4 M of hydrochloride, and were twice extracted with diethylether. The organic phase was dried, filtrated and concentrated with magnesium sulfate to obtain arylbis(triflyl)methane as a solid. No further purification was needed. The yield of each of the arylmethyl triflone is indicated in Table 2, and the physical property of each of the arylmethyl triflone is shown below.

TABLE 2

| arylmethyl triflone | arylbis(triflyl)methane | [yield (%)] |
|---|---|---|
| 2-NaphCH$_2$Tf | 2-NaphCHTf$_2$ | 84 |
| 1-NaphCH$_2$Tf | 1-NaphCHTf$_2$ | 98 |
| 2,4,6-Me$_3$C$_6$H$_2$CH$_2$Tf | 2,4,6-Me$_3$C$_6$H$_2$CHTf$_2$ | 89 |
| 4-CF$_3$C$_6$H$_4$CH$_2$Tf | 4-CF$_3$C$_6$H$_4$CHTf$_2$ | 87 |
| 3,5-(CF$_3$)$_2$C$_6$H$_3$CH$_2$Tf | 3,5-(CF$_3$)$_2$C$_6$H$_3$CHTf$_2$ | 75 |
| C$_6$F$_5$CH$_2$Tf | C$_6$F$_5$CHTf$_2$ | 45 |

Phenylbis(triflyl)methane (Phenylbis(triflyl)methane; J. Org. Chem. 38, 3358, 1973; Heteroatom Chem. 5, 9, 1994): IR (KBr) 2950, 1381, 1242, 1219, 1184, 1102, 806, 695, 660, 608, 585, 507 cm$^{-1}$; $^1$H NMR (CDCl$_3$, 300 MHz) δ 5.97 (s, 1H), 7.54–7.68 (m, 5H); $^{13}$C NMR (CDCl$_3$, 125 MHz) δ 80.7, 119.3, 119.3 (q, J$_{CF}$=329 Hz, 2C, 2CF$_3$), 130.0 (2C), 131.8 (br), 132.9 (2C); $^{9}$F NMR (CDCl$_3$, 282 MHz) −73.8 (s, 6F, 2CF$_3$).

2-naphthylbis(triflyl)methane (2-Naphthylbis(triflyl) methane): IR (KBr) 1393, 1381, 1244, 1213, 1103, 646, 586 cm$^{-1}$; $^1$H NMR (CDCl$_3$, 300 MHz) δ 6.10 (s, 1H), 7.61–7.71 (m, 3H), 7.92–7.99 (m, 2H), 8.03 (d, J=8.4 Hz, 2H); $^{13}$C NMR (CDCl$_3$, 75 MHz) δ 80.9, 116.3, 119.3 (q, J$_{CF}$=329 Hz, 2C, 2CF$_3$), 127.7, 128.0, 128.8, 129.1, 130.1, 132.8, 133.4, 134.7; $^{19}$F NMR (CDCl$_3$, 282 MHz) δ−73.6 (s, 6F, 2CF$_3$); HRMS (EI) calcd for C$_{13}$H$_8$O$_4$F$_6$S$_2$ [M]$^+$ 405.9768, found 405.9761.

1-naphthylbis(triflyl)methane (1-Naphthylbis(triflyl) methane): IR (KBr) 1389, 1383, 1215, 1111, 770, 650, 504 cm$^{-1}$; $^1$H NMR (CDCl$_3$, 300 MHz) δ 6.87 (s, 1H), 7.62–7.80 (m, 4H), 8.02 (d, J=8.4 Hz, 1H), 8.16 (d, J=8.4 Hz, 1H), 8.37 (d, J=7.5 Hz, 1H); $^{13}$C NMR (CDCl$_3$, 75 MHz) δ 74.6, 114.1 (s, 1C, ipso-C), 119.4 (q, J$_{CF}$=328 Hz, 2C, 2CF$_3$), 119.9, 125.4, 127.0, 128.9, 130.1, 131.5, 131.7, 133.8, 134.0; $^{19}$F NMR (CDCl$_3$, 282 MHz) δ −74.2 (s, 6F, 2CF$_3$); HRMS (EI) calcd for C$_{13}$H$_8$O$_4$F$_6$S$_2$ [M]$^+$ 405.9768, found 405.9761.

2,4,6-trimethylphenylbis(triflyl)methane (2,4,6-Trimethylphenylbis(triflyl)methane): IR (KBr) 1397, 1383, 1217, 1119, 1107, 642, 590 cm$^{-1}$; $^1$H NMR (CDCl$_3$, 300 MHz) δ 2.33 (s, 3H), 2.35 (s, 3H), 2.61 (s, 3H), 6.48 (s, 1H), 7.00 (s, 1H), 7.08 (2, 1H); $^{13}$C NMR (CDCl$_3$, 75 MHz) δ 20.2, 21.1, 22.2, 77.7, 115.9, 119.4 (q, J$_{CF}$=328 Hz, 2C, 2CF$_3$), 130.4, 132.2, 140.0, 142.2, 142.6; $^{19}$F NMR (CDCl$_3$, 282 MHz) δ−76.3 (s, 6F, 2CF$_3$); HRMS (EI) calcd for C$_{12}$H$_{12}$O$_4$F$_6$S$_2$ [M]$^+$ 398.0081, found 398.0089.

4-(trifluoromethyl)phenylbis(triflyl)methane (4-(Trifluoromethyl)phenylbis(triflyl)methane): IR (KBr) 1393, 1383, 1327, 1231, 1171, 1136, 1111, 860, 671, 610 cm$^{-1}$; $^1$H NMR (CDCl$_3$, 300 MHz) δ 5.98 (s, 1H), 7.84 (s, 4H); $^{13}$C NMR (CDCl$_3$, 125 MHz) δ 80.4, 120.0 (q, J$_{CF}$=329 Hz, 2C, 2CF$_3$), 123.8 (q, J$_{CF}$=271 Hz, 1C, CF$_3$), 124.2, 127.6 (q, J=4 Hz, 2C), 133.0 (2C), 135.6 (q, J$_{CF}$=33 Hz, 1C); $^{19}$F NMR (CDCl$_3$, 282 MHz) δ−73.5 (s, 6F, 2CF$_3$), −64.7 (s, 3F, CF$_3$); HRMS (EI) calcd for C$_{10}$H$_5$O$_4$F$_9$S$_2$ [M]$^+$ 423.9486, found 423.9471.

3,5-bis(trifluoromethyl)phenylbis(triflyl)methane (3,5-Bis(trifluoromethyl)phenylbis(triflyl)methane): IR (KBr) 1395, 1374, 1285, 1223, 1194, 1179, 1144, 1105, 936, 909, 629, 519 cm$^{-1}$; $^1$H NMR (CDCl$_3$, 300 MHz) δ 6.05 (s, 1H), 8.13 (s, 2H), 8.18 (s, 1H); $^{13}$C NMR (CDCl$_3$, 125 MHz δ 78.9, 119.2 (q, J$_{CF}$=329 Hz, 2C, 2CF$_3$), 122.2 (q, J$_{CF}$=272 Hz, 2C, 2CF$_3$), 122.9, 126.7 (septet, J$_{CF}$=4 Hz), 131.6 (s, 2C), 133.8 (q, J=35 Hz, 2C); $^{19}$F NMR (CDCl$_3$, 282 MHz) δ−73.2 (s, 6F, 2CF$_3$), −64.3 (s, 6F, 2CF$_3$); HRMS (EI) calcd for C$_{11}$H$_4$O$_4$F$_{12}$S$_2$ [M]$^+$ 472.9375, found 472.9372.

Pentafluorophenylbis(triflyl)methane (Pentafluorophenylbis(triflyl)methane): Mp. 86° C. to 87° C.; IR (KBr) 1522, 1501, 1347, 1321, 1198, 1127, 1024, 988, 613 cm$^{-1}$; $^1$H NMR (CDCl$_3$, 300 MHz) δ 6.21 (brs, 1H); $^{13}$C NMR (CDCl$_3$, 125 MHz) δ 70.4, 98.0 (s, 1C, ipso-C), 119.2 (q, J$_{CF}$=330 Hz, 2C, 2CF$_3$), 137.8 (d, J$_{CF}$=258 Hz, 1C, m-C), 138.6 (d, J$_{CF}$=257 Hz, 1C, m-C), 144.7 (d, J$_{CF}$=264 Hz, 1C, p-C), 145.4 (d, J$_{CF}$=262 Hz, 1C o-C), 147.2 (d, J$_{CF}$=262 Hz, 1C, o-C); $^{13}$C NMR (CD$_3$OD (δ 49.0), 125 MHz) δ 56.2, 109.1 (dt, J=6, 19 Hz, 1C, ipso-C), 122.4 (q, J$_{CF}$=324 Hz, 2C, 2CF$_3$), 138.5 (d, J$_{CF}$=250 Hz, 2C, 2m-C), 143.0 (d, J$_{CF}$=251 Hz, 1C, p-C), 150.0 (d, J$_{CF}$=245 Hz, 1C, o-C); $^{19}$F NMR (CDCl$_3$, 282 MHz) δ−157.9 (dt, J=6.2, 21.5 Hz, 1F, m-F), −156.8 (dt, J=6.2, 21.5 Hz, 1F, m-F), −142.6 (tt, J=5.9, 21.5 Hz, 1F, p-F), −140.3 (br, 1F, o-F), −127.7 (ddd, J=5.9, 15.2, 21.5 Hz, 1F, o-F), −75.2 (s, 6F, 2CF$_3$); HRMS (EI) calcd for C$_9$HO$_4$F$_{11}$S$_2$ [M]$^+$ 445.9141, found 445.9137.

EXAMPLE 4

Nucleophilic Substitution Specific to the Para Position of Pentafluorophenylbis(triflyl)methane As it is described in Table 2 that the yield of pentafluorophenylbis(triflyl)methane is 45%, it was revealed that when pentafluorophenylbis(triflyl)methane is produced using a pentafluorophenylmethyl triflone, both of pentafluorophenylbis(triflyl)methane and 4-tert-butyl-2,3,5,6-tetrafluorophenylbis(triflyl)methane can be obtained at a ratio of 1:1 (45% yield, respectively). However, it was found out that when 1.0 equivalent weight of t-BuLi and 0.5 equivalent weight of Tf$_2$O are used, the production of 4-tert-butyl-2,3,5,6-tetrafluorophenylbis(triflyl)methane is completely suppressed, and pentafluorophenylbis(triflyl)methane can be obtained at 95% yield with Tf$_2$O as a base. Consequently, the reactions of pentafluorophenylbis(triflyl)methane with the various types of alkyl lithium reagents were examined, in order to determine the generality and range of the nucleophilic substitution specific to the para position of pentafluorophenylbis(triflyl)methane. Table 3 shows the types of alkyl lithium reagents, the reaction conditions and the yield of the para position substituents of pentafluorophenylbis(triflyl)methane. The para position substituents of pentafluorophenylbis(triflyl)methane shown in Table 3 are obtained by washing the reaction product obtained by reacting pentafluorophenylbis(triflyl)methane with alkyl lithium reagent, with a hydrochloric solution. The "Bn" shown in Table 3 represents a benzyl group.

TABLE 3

| RLi (equivalent weight) | Condition | Yield (%) |
|---|---|---|
| t-BuLi (3) | −78° C., 1 h | 87 |
| BuLi (3) | −78° C., 1 h | >95 |
| BnLi (5) | −78° C., 6 h | 83 |
| PhLi (3) | −78° C. to rt, 1 day | >95 |
| 3,4,5-F$_3$C$_6$H$_2$Li (5) | −20° C. to rt, 3 h | 75 |
| 3,5-(CF$_3$)$_2$C$_6$H$_3$Li (5) | −20° C. to rt, 3 h | 70 |

EXAMPLE 5

Synthesis of {4-(pentafluorophenyl)-2,3,5,6-tetrafluorophenyl}bis(triflyl)methane Synthesis of 4-methylperfluorobiphenyl;

A diethylether solution of methyl lithium (13 mL, 15 mmol) was dropped for 0.5 hour to a THF (50 mL) solution of perfluorobiphenyl (10 g, 30 mmol), at −78° C. under argon atmosphere. Then, after the solution was stirred at the same temperature for 2 hours, it was further stirred at room temperature for 2 hours. Water was added to stop the reaction, diethylether was used for extraction, and its organic phase was dried with magnesium sulfate. After filtration was conducted, the solvent was removed under reduced pressure, and a mixture of 4-methylperfluorobiphenyl, 4,4'-dimethylperfluorobiphenyl and perfluorobiphenyl (molar ratio, 30:3:67) was obtained as a crude product.

Synthesis of 4-(bromomethyl)perfluorobiphenyl;

A mixed solution of a mixture comprising the 4-methylperfluorobiphenyl mentioned above, an N-bromo succinic imide (NBS) (26.7 g, 150 mmol), AIBN (0.99 g, 6 mmol) andacarbon tetrachloride (100 mL) was subjected to heating under reflux for 1 week. During this process, the progress of the reaction was confirmed by TLC, and NBS and AIBN were added on a timely basis. Ultimately, 285 mmol NBS and 15 mmol AIBN were added to the solution. After the reaction was completed, the solution was cooled to room temperature, and the solvent was removed under reduced pressure. The crude product was purified by silica gel column chromatography (developing solvent: hexane-ethyl acetate=100:1), and the 4-(bromomethyl)perfluorobiphenyl (7.36 g, 18 mmol, total yield from methyl lithium 60%) was isolated.

$^1$H NMR (CDCl$_3$, 300 MHz) δ 4.58 (s, 2H, CH$_2$Br); $^{19}$F NMR (CDCl$_3$, 282 MHz) δ−138.02 (dd, J=10.6, 19.8 Hz, 2F), −138.56 (dt, J=9.1, 20.3 Hz, 2F), −142.36 (dd, J=10.6, 19.8 Hz, 2F), −150.59 (t, J=20.3 Hz, 1F), −161.08 (dt, J=7.1, 20.3 Hz, 2F).

Synthesis of {4-(pentafluorophenyl)-2,3,5,6-tetrafluorophenyl}(triflyl)methane;

4-(bromomethyl)perfluorobiphenyl (3.68 g, 9 mmol) and sodium trifluoromethane sulfinate (1.69 g, 10.8 mmol) were dissolved in propionitrile (30 mL), and the resultant solution was subjected to heating under reflux for 12 hours. After the reaction, the solution was cooled to room temperature, and water was added for extraction with ethyl acetate. The organic phase was dried with magnesium sulfate, filtrated, and the solvent was removed under reduced pressure. The crude product was purified by silica gel column chromatography (hexane-ethyl acetate=20:1 to 8:1 to 1:1), and the aimed {4-(pentafluorophenyl)-2,3,5,6-tetrafluorophenyl}(triflyl)methane (3.91 g, 8.46 mmol, 94% yield) was isolated.

$^1$H NMR (CDCl$_3$, 300 MHz) δ 4.75 (s, 2H, CH$_2$Tf); $^{19}$F NMR (CDCl$_3$, 282 MHz) δ−78.24 (s, 3F, CF$_3$), −136.82 to −136.62 (m, 1F), −137.72 (dd, J=10.7, 18.3 Hz, 2F), −138.84 (dd, J=10.7, 18.3 Hz, 2F), −149.69 (t, J=21.3 Hz, 1F), −160.63 (dt, J=6.1, 21.3 Hz, 2F).

Synthesis of {4-(pentafluorophenyl)-2,3,5,6-tetrafluorophenyl}bis(triflyl)methane;

A tert-butyl magnesium chloride (5 mL, 10 mmol, 2.0 M diethylether solution) was added to a diethylether (120 mL) solution dissolved with {4-(pentafluorophenyl)-2,3,5,6-tetrafluorophenyl}(triflyl)methane (4.6 g, 10 mmol), at −78° C. under argon atmosphere. After the reaction solution was stirred for 0.5 hour at −78° C., it was further stirred for 0.5 hour at 0° C. Then, the solution was cooled again to −78° C., trifluoromethane sulfonic acid anhydride (0.84 mL, 5 mmol) was added, and the resultant solution was stirred for 2 hours at room temperature. Further, tert-butyl magnesium chloride (3.75 mL, 7.5 mmol, 2.0 M diethylether solution) was added at −78° C. After the reaction solution was stirred at −78° C. for 0.5 hour, it was stirred at 0° C. for 0.5 hour. The solution was cooled again to −78° C., trifluoromethane sulfonic acid anhydride (0.84 mL, 5 mmol) was added, and the resultant solution was stirred for 2 hours at room temperature. After the reaction was completed, water was added, further neutralized with 1 M hydrochloric acid-water, and the water phase was washed with hexane. Then, said water phase was acidified with 4 M hydrochloric acid water, and extracted with diethylether. The organic phase was dried with magnesium sulfate, filtrated, and the solvent was removed under reduced pressure. The crude product was sublimated (8 to 9 Pa, 150° C., and the aimed {4-(pentafluorophenyl)-2,3,5,6-tetrafluorophenyl}bis(triflyl)methane (2.79 g, 4.7 mmol, 47% yield) was isolated.

$^1$H NMR (CDCl$_3$, 300 MHz) δ 6.32 (s, 1H, CH), $^{19}$F NMR (CDCl$_3$, 282 MHz) δ−75.1 (s, 6F, 2CF$_3$), −127.72 to −127.58 (m, 1F), −133.43 (dt, J=10.2, 21.3 Hz, 1F), −134.60 (dt, J=9.4, 21.3 Hz, 1F), −137.08 to −137.35 (m, 2F), −140.07 (br, 1F), −148.38 (t, J=21.3 Hz, 1F), −160.01 (dt, J=6.2, 21.3 Hz, 2F).

EXAMPLE 6

Synthesis of Lithium Pentafluorophenylbis(triflyl)methide

The pentafluorophenylbis(triflyl)methane obtained from Example 3 (1 mmol) and LiOH·H$_2$O (1 mmol) were dissolved in a diethylether (10 mL), the resultant solution was stirred at room temperature for 12 hours, then concentrated and dried to obtain a white powder, lithium pentafluorophenylbis(triflyl)methide (100% yield). The physical property of this lithium pentafluorophenylbis(triflyl)methide obtained is as follows.

Lithium pentafluorophenylbis(triflyl)methide (Lithium Pentafluorophenylbis(triflyl)methide): $^{13}$C NMR (CD$_3$OD, 125 MHz) δ 56.1, 109.0 (dt, J=4, 19 Hz, 1C, ipso-C), 122.3 (q, J$_{CF}$=324 Hz, 2C, 2CF$_3$), 138.5 (d, J$_{CF}$=247 Hz, 2C, 2m-C), 143.0 (d, J$_{CF}$=251 Hz, 1C, p-C), 149.5 (d, J$_{CF}$=245 Hz, 2C, 2o-C).

EXAMPLE 7

Synthesis of Lithium{4-(pentafluorophenyl)-2,3,5,6-tetrafluorophenyl}bis(triflyl)methide The {4-(pentafluorophenyl)-2,3,5,6-tetrafluorophenyl}bis(triflyl)methane obtained from Example 5 (1 mmol) and LiOH·H$_2$O (1 mmol) were dissolved in a diethylether (10 mL), the resultant solution was stirred at room temperature for 12 hours, then concentrated and dried to obtain a white solid, lithium{4-(pentafluorophenyl)-2,3,5,6-tetrafluorophenyl}bis(triflyl)methide (100% yield).

EXAMPLE 8

Synthesis of Silver (I) Pentafluorophenylbis(triflyl)methide

Ag$_2$CO$_3$ (66 mg, 0.24 mmol) was added to an aqueous solution (3 mL) of pentafluorophenylbis(triflyl)methane (0.20 g, 0.40 mmol) in a reaction flask wherein light was shut out by an aluminum foil. The solution was stirred at room temperature for 12 hours, then filtrated if there were any solid remaining, followed by concentration. A white solid of silver (I) pentafluorophenylbis(triflyl)methide was obtained thereby (99% yield or more). The physical property of this silver (I) pentafluorophenylbis(triflyl)methide obtained is as follows.

Silver (I) pentafluorophenylbis(triflyl)methide (Silver(I) Pentafluorophenylbis(triflyl)methide): $^{19}$F NMR (CDCl$_3$, 282 MHz) δ−162.6 (dt, J=7.6, 21.4 Hz, 2F, 2m-F), −150.6 (t, J=21.4 Hz, 1F, p-F), −134.7−134.6 (m, 2F, 2o-F), −79.5 (s, 6F, 2CF$_3$).

EXAMPLE 9

Synthesis of Scandium (III) Pentafluorophenylbis(triflyl)methide (Part 1)

Sc$_2$O$_3$ (21 mg, 0.155 mmol) and pentafluorophenylbis(triflyl)methane (0.277 g, 0.62 mmol) were subjected to heating under reflux in water (0.5 mL) for 12 hours. Then, the unreacted Sc$_2$O$_3$ was removed by filtration and condensation was conducted. The crude product obtained was washed with chloroform, the unreacted pentafluorophenylbis(triflyl)methane was removed, pressure was reduced by a vacuum pump, and then dried at 100° C. to obtain a white powder of scandium (III) pentafluorophenylbis(triflyl)methide (50% yield).

EXAMPLE 10

Synthesis of Scandium (III) Pentafluorophenylbis(triflyl)methide (Part 2)

The silver (I) pentafluorophenylbis(triflyl)methide obtained from Example 8 (0.19 g, 0.34 mmol) and Sc (III) $Cl_3 \cdot (H_2O)_6$ (29 mg, 0.11 mmol) were stirred in a diethylether (3 mL) at room temperature for 12 hours. Then, silver chloride was removed by filtration and condensation was conducted. The unreacted pentafluorophenylbis(triflyl)methane was removed, pressure was reduced by a vacuum pump, and then dried at 100° C. to obtain a white powder of scandium (III) pentafluorophenylbis(triflyl)methide (50% yield). The physical property of the scandium (III) pentafluorophenylbis(triflyl)methide obtained from the present Example and Example 9 is as follows.

Scandium (III) pentafluorophenylbis(triflyl)methide (Scandium (III) Pentafluorophenylbis(triflyl)methide): Mp.> 250° C. (decomposed); $^{13}$C NMR (CD$_3$OD (δ49.0), 125 MHz) δ 56.2, 109.0 (dt, $J_{CF}$=2, 20 Hz, 1C, ipso-C), 122.3 (q, $J_{CF}$=324 Hz, 2C, 2CF$_3$), 137.8 (d, $J_{CF}$=247 Hz, 2C, 2m-C), 142.3 (d, $J_{CF}$=251 Hz, 1C, p-C), 148.9 (d, $J_{CF}$=245 Hz, 2C, 2o-C); $^{19}$F NMR (CD$_3$OD, 282 MHz) δ−166.4 (dt, J=6.1, 21.3 Hz, 2F, 2m-F), −155.9 (t, J=21.3 Hz, 1F, p-F), −134.9 to −134.9 (m, 2F, 2o-F), −80.9 (s, 6F, 2CF$_3$).

EXAMPLE 11

Production of Polystyrene-Supported Pentafluorophenylbis(triflyl)methane

A lithium pentafluorophenylbis(triflyl)methide was supported on a 4-bromopolystyrene resin, and a polystyrene-supported pentafluorophenylbis(triflyl)methane was produced in the following manner (Chemical formula 7). 4-bromopolystyrene resin (a copolymer from 2% divinylbenzene, 200 to 400 mesh, bromine supporting rate 3.03 mmol/g; Tokyo Kasei Kogyo Co., Ltd.) (0.33 g, 1 mmol) was swelled in benzene (5 mL), and 1.6 M of hexane solution of butyl lithium (1.88 mL, 3 mmol) was added therein under an argon atmosphere at room temperature. This mixed solution was heated to 60° C. (bath temperature), stirred for 3 hours, then once returned to room temperature. Only the solution part of the mixed solution was removed by using a syringe. Benzene (1 mL) and THF (1 mL) were added to the remaining resin, the solution was cooled to 0° C., and the lithium pentafluorophenylbis(triflyl)methide obtained from Example 5 (1.36 g, 3 mmol) was added. Next, the reaction solution was warmed to room temperature and stirred for 2 hours, and further stirred for 12 hours at 70° C. (bath temperature). Then, the reaction solution was cooled to 0° C., and 4M hydrochloric acid (10 mL) was added therein. Subsequently, resin was collected by suction filtration using a filter paper, and the resin was washed sequentially by using distilled water (10 mL), distilled water (5 mL)-THF (5 mL) mixed solution, THF (10 mL) and diethylether (10 mL). Finally, the resin was dried for 5 hours at 80° C. under reduced pressure of 1 torr, and a polystyrene-supported pentafluorophenylbis(triflyl)methane (0.413 g) which is a solid catalyst was obtained.

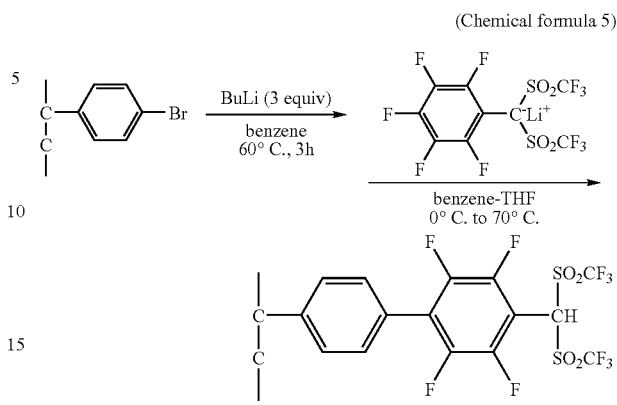

(Chemical formula 5)

The Bronsted acid supporting rate obtained from the content of fluorine by an elementary analysis of the polystyrene-supported pentafluorophenylbis(triflyl)methane obtained was 1.06 mmol/g. The physical property of the polystyrene-supported pentafluorophenylbis(triflyl)methane is as follows.

Polystyrene-supported pentafluorophenylbis(triflyl)methane (Polysthlene resin, cross-linked with 2% divinylbenzene with Pentafluorophenylbis(triflyl)methane): IR (KBr) 1475, 1352, 1194, 1119, 1022, 976, 700 612 cm$^{-1}$.

EXAMPLE 12

Production of Polystyrene-Supported {4-(pentafluorophenyl)-2,3,5,6-tetrafluorophenyl}bis(triflyl)methane A lithium {4-(pentafluorophenyl)-2,3,5,6-tetrafluorophenyl}bis(triflyl)methide was supported on a 4-bromopolystyrene resin, and a polystyrene-supported {4-(pentafluorophenyl)-2,3,5,6-tetrafluorophenyl}bis(triflyl) methane was produced in the following manner (Chemical formula 8). 4-bromopolystyrene resin (a copolymer from 2% divinylbenzene, 200 to 400 mesh, bromine supporting rate 3.03 mmol/g; Tokyo Kasei Kogyo Co., Ltd.) (0.33 g, 1 mmol) was swelled in benzene (5 mL), and 1.6 M hexane solution of butyl lithium (1.88 mL, 3 mmol) was added therein under an argon atmosphere at room temperature. This mixed solution was heated to 60° C. (bath temperature), stirred for 3 hours, then once returned to room temperature. Only the solution part of the mixed solution was removed by using a syringe. Benzene (3 mL) and THF (1 mL) were added to the remaining resin, the solution was cooled to 0° C., and the lithium{4-(pentafluorophenyl)-2,3,5,6-tetrafluorophenyl}bis(triflyl)methide obtained from Example 7 (1.78 g, 3 mmol) was added. Next, the reaction solution was warmed to room temperature and stirred for 0.5 hour, and further stirred for 12 hours at 70° C. (bath temperature). Then, the reaction solution was cooled to 0° C., and 4M hydrochloric acid (10 mL) was added therein. Subsequently, resin was collected by suction filtration using a filter paper, and the resin was washed sequentially by using distilled water (10 mL), distilled water (5 mL)-THF (5 mL) mixed solution, THF (10 mL) and diethylether (10 mL). Finally, the resin was dried for 5 hours at 80° C. under reduced pressure of 1 torr, and a polystyrene-supported {4-(pentafluorophenyl)-2,3,5,6-tetrafluorophenyl}bis(triflyl)methane (0.440 g) which is a solid catalyst was obtained.

(Chemical formula 6)

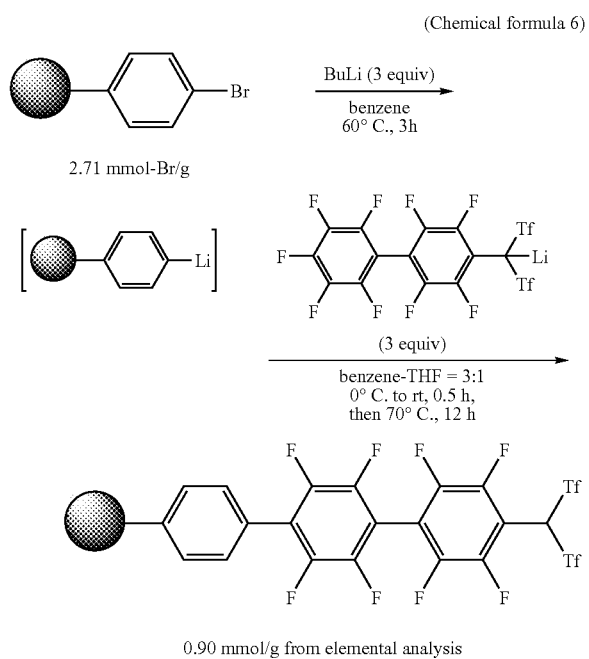

0.90 mmol/g from elemental analysis

The Bronsted acid supporting rate obtained from the content of fluorine by an elementary analysis of the polystyrene-supported {4-(pentafluorophenyl)-2,3,5,6-tetrafluorophenyl}bis(triflyl)methane obtained was 0.90 mmol/g.

EXAMPLE 13

Mukaiyama Aldol Reaction

The polystyrene-supported pentafluorophenylbis(triflyl)methane obtained from Example 11 was used as a solid catalyst, and a Mukaiyama aldol reaction wherein aldol is obtained from trimethylsilylenolether and benzaldehyde, was conducted in the following manner (Chemical formula 9). The solid catalyst mentioned above (16 mg, Bronsted acid supporting rate 1.06 mmol/g) was added to 1 mL of toluene, the solution was cooled to −78° C., trimethylsilylenolether of acetophenone (0.12 mL, 0.6 mmol) and benzaldehyde (0.05 mL, 0.5 mmol) were added therein, and then stirred for 7 hours at −78° C. After the reaction, 2 to 3 drops of triethylamine was added at −78° C. and returned to room temperature. Next, resin was collected by vacuum filtration. Further, the filtrate was concentrated, 1 M hydrochloric acid (1 mL) and THF (1 mL) were added at room temperature and stirred for 15 minutes, then the trimethylsilylether of aldol was converted to alcohol. After a normal posttreatment, separation and purification by silica gel column chromatography (hexane:ethyl acetate=8:1 to 4:1) was conducted to obtain aldol. The yield of the aldol obtained (109.7 mg, 0.49 mmol) was 97%. The resin was washed sequentially by using 4 M of hydrochloric acid (1 mL), distilled water (1 mL), distilled water (0.5 mL)-THF (0.5 mL) mixed solution, THF (1 mL) and diethylether (1 mL), then dried. A solid catalyst was recovered at a yield of almost 100%.

(Chemical formula 7)

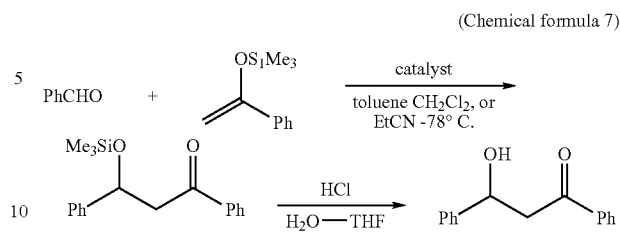

The same reaction as described above was conducted, except that in place of the polystyrene-supported pentafluorophenylbis(triflyl)methane mentioned above, 16 mg of Nafion SAC-13 (DuPont) was used as the conventionally known polymer-supported Bronsted acid catalyst. The yield of aldol obtained was almost the same as when the solid catalyst mentioned above (16 mg, Bronsted acid supporting rate 1.06 mmol/g) was used. Further, the recovery rate of the catalyst was 100%.

EXAMPLE 14

Hosomi-Sakurai Allylation Reaction

The polystyrene-supported pentafluorophenylbis(triflyl)methane obtained from Example 11 was used as a solid catalyst, and a Hosomi-Sakurai allylation reaction wherein allyl alcohol is obtained from allyltrimethylsilane and benzaldehyde, was conducted in the following manner (Chemical formula 10). Allyltrimethylsilane (0.48 mL, 3 mmol) and the solid catalyst mentioned above (57 mg, Bronsted acid supporting rate 1.06 mmol/g) were added to 0.41 mL of dichloromethane, and stirred at room temperature for 30 minutes. Subsequently, the solution was cooled to −40° C., and a dichloromethane solution of benzaldehyde (0.2 mL, 2 mmol) was dropped slowly for 30 minutes. After dropping, the solution was further stirred for 1 hour at −40° C. After the reaction, 2 to 3 drops of triethylamine was added at −40° C. and returned to room temperature. Next, resin was collected by vacuum filtration. Further, the filtrate was concentrated, 1 M hydrochloric acid (2.5 mL) and THF (2.5 mL) were added at room temperature and stirred for 30 minutes, then the trimethylsilylether of homoallyl alcohol was converted to alcohol. After a normal posttreatment, separation and purification by silica gel column chromatography (hexane:ethyl acetate=10:1 to 5:1) was conducted to obtain homoallyl alcohol (267 mg, 1.8 mmol). The yield of the homoallyl alcohol obtained was 90%. The resin was washed sequentially by using 4 M hydrochloric acid (1 mL), distilled water (1 mL), distilled water (0.5 mL)-THF (0.5 mL) mixed solution, THF (1 mL) and diethylether (1 mL) then dried. A solid catalyst was recovered at a yield of almost 100%.

(Chemical formula 8)

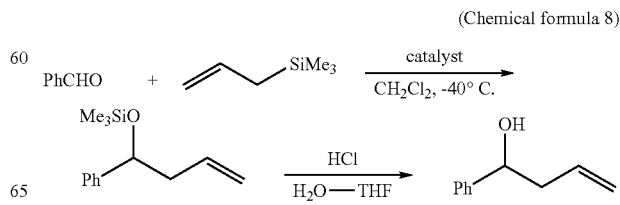

The same reaction as described above was conducted, except that in place of the polystyrene-supported pentafluorophenylbis(triflyl)methane mentioned above, 57 mg of Nafion SAC-13 (DuPont) was used as a conventionally known polymer-supported Bronsted acid catalyst. The yield of allyl alcohol was only 2%. Further, the recovery rate of the catalyst was 100%. Based on these results, it was found out that the catalytic activity of the polystyrene-supported pentafluorophenylbis(triflyl)methane of the present invention is much more higher compared to that of the existing polymer-supported Bronsted acid catalyst.

EXAMPLE 15

Acylation Reaction of Alcohol

The polystyrene-supported pentafluorophenylbis(triflyl)methane obtained from Example 11 was used as a solid catalyst, and an acylation reaction wherein ester is obtained from menthol and benzoic acid, was conducted in the following manner (Chemical formula 11). A 1-menthol (157 mg, 1 mmol), a benzoic anhydride (340 mg, 1.5 mmol) and the solid catalyst mentioned above (65 mg, Bronsted acid supporting rate: 1.06 mmol/g) were added to 4.8 mL of acetonitrile, and the solution was stirred for 17 hours at 27° C. After the reaction, resin was collected by vacuum filtration, and separatory extraction was conducted to the filtrate by using water (5 mL) and hexane (10 mL). After a normal posttreatment was conducted to the organic phase, separation and purification by silica gel column chromatography (hexane:ethyl acetate=10:1) was conducted to obtain ester (260 mg, 1 mmol). The yield of the ester obtained was >99%. The resin was washed sequentially by using 4 M hydrochloric acid (1 mL), distilled water (1 mL), distilled water (0.5 mL)-THF (0.5 mL) mixed solution, THF (1 mL) and diethylether (1 mL), then dried. A solid catalyst was recovered at a yield of almost 100%.

(Chemical formula 9)

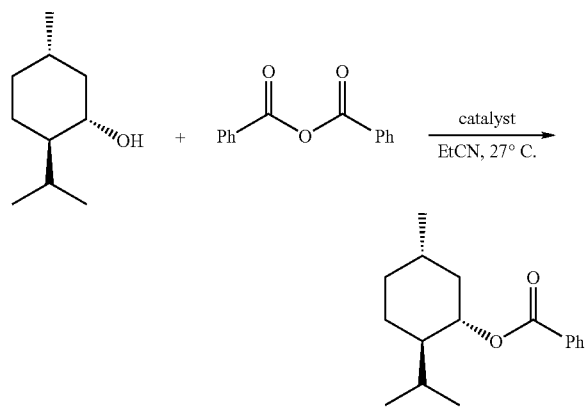

The same reaction as described above was conducted, except that in place of the polystyrene-supported pentafluorophenylbis(triflyl)methane mentioned above, 57 mg of Nafion SAC-13 (DuPont) was used as a conventionally known polymer-supported Bronsted acid catalyst. The yield of ester was 0%. Further, the recovery rate of the catalyst was 100%. Based on these results, it was found out that reactions that can not be conducted by the known polymer-supported Bronsted acid catalyst can be conducted by the polystyrene-supported pentafluorophenylbis(triflyl)methane of the present invention.

EXAMPLE 16

Acetalyzation Reaction of Ketone

The polystyrene-supported pentafluorophenylbis(triflyl)methane obtained from Example 11 was used as a solid catalyst, and an acetalyzation reaction wherein dimethylacetal is obtained from benzylacetone and methyl orthoformate, was conducted in the following manner (Chemical formula 12). Toluene (2 mL) was added to the solid catalyst mentioned above (10.6 mg, 0.5 mol %, 1.06 mmol/g), and the solution was stirred (swelled) for 30 minutes at room temperature. Then, the solution was cooled to 0° C., and benzylacetone (0.30 mL, 2.0 mmol) and methyl orthoformate (0.26 mL, 0.24 mmol) were added therein. After stirring the solution for 20 minutes at 0° C., resin was collected by vacuum filtration, and separatory extraction was conducted to the filtrate by using water (5 mL) and hexane (10 mL). After a normal posttreatment was conducted to the organic phase, separation and purification by silica gel column chromatography (hexane:ethyl acetate=10:1) was conducted to obtain acetal (388 mg, 2 mmol). The yield of the acetal obtained was >99%. The resin was washed sequentially by using 4 M hydrochloric acid (1 mL), distilled water (1 mL), distilled water (0.5 mL)-THF (0.5 mL) mixed solution, THF (1 mL) and diethylether (1 mL), then dried. A solid catalyst was recovered at a yield of almost 100%.

(Chemical formula 10)

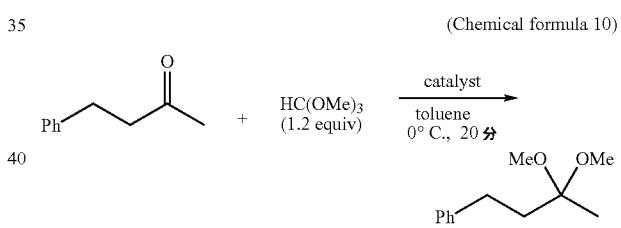

The same reaction as described above was conducted, except that in place of the polystyrene-supported pentafluorophenylbis(triflyl)methane mentioned above, 10.6 mg of Nafion SAC-13 (DuPont) was used as a conventionally known polymer-supported Bronsted acid catalyst. The yield of acetal was only 16%. Further, the recovery rate of the catalyst was 100%. Based on these results, it was found out that the catalytic activity of the polystyrene-supported pentafluorophenylbis(triflyl)methane of the present invention is much more higher compared to that of the existing polymer-supported Bronsted acid catalyst.

INDUSTRIAL APPLICABILITY

The polymer-supported arylbis(perfluoroalkylsulfonyl)methane of the present invention such as the polystyrene-supported arylbis(perfluoroalkylsulfonyl)methane and the like can be used for most of the reactions that progress with Bronsted acid or Lewis acid catalyst, and can also easily progress the reactions that were difficult to be progressed with the use of conventional catalysts, since a super strong acid, arylbis(perfluoroalkylsulfonyl)methane, is supported on a resin polymer such as polystyrene resin and the like.

Moreover, since the recovery rate of the catalyst is high and the catalyst is easy to recycle, its versatility is very high. Since this catalyst is an organic acid that does not contain metal, it is excellent from the point of toxicity, environment and others. According to the present invention, a super strong acid to become a homogeneous catalyst can be supported for the first time, to a polymer resin that shows excellent swelling ability to organic solvents (for example, aromatic-based solvent, halogen-based solvent, ether-based solvent and the like), thereby attaining a high catalytic activity to organic reactions by various kinds of acid catalysts.

What is claimed is:

1. A polymer-supported arylbis(perfluoroalkylsulfonyl)methane wherein the arylbis(perfluoroalkylsulfonyl)methane is represented by formula 1

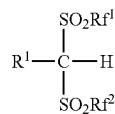

formula 1 wherein $R^1$ shows a substituted or unsubstituted aryl group, $Rf^1$ and $Rf^2$ are independent to each other and show a perfluoroalkyl group, and is supported on an organic polymer resin capable of generating an anion with a basic reactant.

2. The polymer-supported arylbis(perfluoroalkylsulfonyl)methane according to of claim 1, wherein the arylbis(perfluoroalkylsulfonyl)methane represented by formula 1 is supported on an organic polymer by a reaction of an electrophilic substituent of its aryl group with an anion of an organic polymer.

3. The polymer-supported arylbis(perfluoroalkylsulfonyl)methane according to claim 2, wherein the $Rf^1$ and $Rf^2$ in formula 1 are both a trifluoromethyl group.

4. The polymer-supported arylbis(perfluoroalkylsulfonyl)methane according to claim 2, wherein the $R^1$ in formula 1 is a phenyl group, a naphthyl group, a 2,4,6-trimethylphenyl group, a 4-(trifluoromethyl)phenyl group, a 3,5-bis(trifluoromethyl)phenyl group, a pentafluorophenyl group or a perfluorobiphenyl group.

5. The polymer-supported arylbis(perfluoroalkylsulfonyl)methane according to claim 2, wherein the arylbis(perfluoroalkylsulfonyl)methane is a phenylbis(triflyl)methane, a 2-naphthylbis(triflyl)methane, a 1-naphthylbis(triflyl)methane, a 2,4,6-trimethylphenylbis(triflyl)methane, a 4-(trifluoromethyl)phenylbis(triflyl)methane, a 3,5-bis(trifluoromethyl)phenylbis(triflyl)methane, a pentafluorophenylbis(triflyl)methane or a {4-(pentafluorophenyl)-2,3,5,6-tetrafluorophenyl}bis(triflyl)methane.

6. A method for producing a polymer-supported arylbis(perfluoroalkylsulfonyl)methane wherein said method is a method for producing the polymer-supported arylbis(perfluoroalkylsulfonyl)methane according to claim 1, wherein a resin polymer capable of generating an anion with a basic reactant is reacted with a metallic salt of arylbis(perfluoroalkylsulfonyl)methane represented by formula 2

wherein $R^2$ shows an aryl group having an electrophilic substituent, $Rf^1$ and $Rf^2$ are independent to each other and show a perfluoroalkyl group.

7. The method for producing the polymer-supported arylbis(perfluoroalkylsulfonyl)methane according to claim 6, wherein a haloalkyl resin polymer is used as the resin polymer capable of generating an anion with a basic reactant.

8. The method for producing the polymer-supported arylbis(perfluoroalkylsulfonyl)methane according to claim 7, wherein a halogeno polystyrene resin is used as the haloalkyl resin polymer.

9. The method for producing the polymer-supported arylbis(perfluoroalkylsulfonyl)methane according to claim 8, wherein a 4-bromopolystyrene resin is used as the halogeno polystyrene resin.

10. The method for producing the polymer-supported arylbis(perfluoroalkylsulfonyl)methane according to claim 6, wherein the metallic salt of arylbis(perfluoroalkylsulfonyl)methane is any one of the metallic salts selected from alkaline metallic element, alkaline earth metallic element, transition metallic element, boron, silicon, aluminum, tin, zinc or bismuth.

11. The method for producing the polymer-supported arylbis(perfluoroalkylsulfonyl)methane according to claim 10, wherein the transition metallic element is any one of the metallic elements selected from scandium, yttrium, lanthanoid, copper, silver, titanium, zirconium or hafnium.

12. The method for producing the polymer-supported arylbis(perfluoroaklylsulfonyl)methane according to claim 6, wherein the metallic salt of arylbis(perfluoroalkylsulfonyl)methane is a lithium salt of pentafluorobis(trifluoromethylsulfone).

13. The method for producing the polymer-supported arylbis(perfluoroalkylsulfonyl)methane according to claim 6, wherein a butyl lithium is used as the basic reactant.

14. The method for producing the polymer-supported arylbis(perfluoroalkylsulfonyl)methane according to claim 6, wherein a mixture of benzene and tetrahydrofuran is used as the solvent.

15. A method for synthesizing an organic compound wherein the method is a method for synthesizing an organic compound by using a catalyst having as an active ingredient the metallic salt of polymer-supported arylbis(perfluoroalkylsulfonyl)methane according to claim 1, wherein a catalytic reaction is conducted in a solvent under the presence of said catalyst.

16. The method for synthesizing the organic compound according to claim 15, wherein the catalytic reaction is an acetalyzation reaction, an acylation reaction of alcohol, an aldol-type reaction, an allylation reaction, a Diels-Alder reaction, a Friedel-Crafts reaction, a Mannich reaction, a glycosilation reaction, an esterification reaction, an ene reaction or a cationic polymerization reaction.

17. The method for synthesizing an organic compound according to claim 15, wherein the catalyst according to claim 15 is a Bronsted acid catalyst.

* * * * *